US008529255B2

(12) United States Patent
Poirier et al.

(10) Patent No.: US 8,529,255 B2
(45) Date of Patent: Sep. 10, 2013

(54) DENTAL PROSTHESIS SYSTEM (75) Inventors: Michel Poirier, Ste-Agathe-des-Monts (CA); Eric Wagnac, Montréal (CA)

(73) Assignee: V2R Biomedical Inc, Saint-Jérôme, Québec (CA)

( * ) Notice: Subject to any disclaimer, the term of this patent is extended or adjusted under 35 U.S.C. 154(b) by 147 days.

(21) Appl. No.: 12/689,056

(22) Filed: Jan. 18, 2010

(65) Prior Publication Data
US 2010/0183998 A1     Jul. 22, 2010

Related U.S. Application Data (60) Provisional application No. 61/145,264, filed on Jan. 16, 2009.

(51) Int. Cl.
*A61C 19/04* (2006.01)

(52) U.S. Cl.
USPC .......................................................... 433/72

(58) Field of Classification Search
USPC ..................... 433/72–76, 167–174
See application file for complete search history.

(56) References Cited

U.S. PATENT DOCUMENTS

| | | | |
|---|---|---|---|
| 3,748,739 A * | 7/1973 | Thibert | 433/173 |
| 5,221,204 A * | 6/1993 | Kruger et al. | 433/173 |
| 5,320,529 A * | 6/1994 | Pompa | 433/76 |
| 5,554,027 A * | 9/1996 | Brånemark | 433/172 |
| 5,725,376 A * | 3/1998 | Poirier | 433/172 |
| 6,382,975 B1 * | 5/2002 | Poirier | 433/173 |
| 2002/0137003 A1 * | 9/2002 | Knapp | 433/76 |
| 2002/0177104 A1 * | 11/2002 | Klein et al. | 433/173 |
| 2005/0019727 A1 * | 1/2005 | McGlumphy et al. | 433/173 |
| 2005/0170311 A1 * | 8/2005 | Tardieu et al. | 433/76 |
| 2006/0093988 A1 * | 5/2006 | Swaelens et al. | 433/76 |
| 2006/0223029 A1 * | 10/2006 | Berger | 433/172 |
| 2007/0160953 A1 * | 7/2007 | Tardieu | 433/173 |

FOREIGN PATENT DOCUMENTS

WO    WO 2008052586 A1 *    5/2008

* cited by examiner

*Primary Examiner* — Cris L Rodriguez
*Assistant Examiner* — Matthew Saunders
(74) *Attorney, Agent, or Firm* — Norton Rose Fulbright LLP (57) ABSTRACT

A dental prosthesis system and a method of using same having a prosthesis, a primary bar, and a base-plate. The primary bar is adapted to be received on the implants and to be used as a superstructure for supporting the prosthesis and/or a verification jig. The base-plate has a shape adapted to be received on the patient's gum surface, having at least one hole each in alignment with a corresponding one of the aperture of the primary bar when the primary bar is seated on the base-plate, each hole of the base-plate correspond to the position of each implant hole, the base-plate supporting the primary bar to form a drilling guide for guiding the drilling of implants holes in the patient's jawbone, an impression matrix for creating a physical model of the patient's mouth with implants, and/or a superstructure when removable cylinders are attached to the primary bar.

11 Claims, 6 Drawing Sheets

DENTAL PROSTHESIS SYSTEM

CROSS-REFERENCE TO RELATED APPLICATION

This patent application claims priority on U.S. Provisional Patent Application No. 61/145,264, filed on Jan. 16, 2009.

TECHNICAL FIELD

The present application relates to a dental prosthesis system comprising a drilling guide, a prosthesis, a primary bar, and a base-plate.

BACKGROUND ART

The use of dental prostheses with dental implants secured in the upper or lower jawbone is well known in the art. Accurate placement of the implants within the jawbone is a difficult task. The dental surgeon typically has difficulty deciding on a drilling axis for the implants since the ideal position for the implants should be decided with knowledge of the jawbone structure into which the implant is to be inserted, and with knowledge of the position within the jawbone structure of the nerve tissue, the gum surface and the required position and dimensions of the false teeth or dentures to be supported by the dental implant.

The conventional surgical procedure for installing one, implant-supported, prosthetic tooth includes drilling a properly positioned hole in the jawbone of the patient, inserting the implant in the hole, and attaching the prosthetic tooth to the implant. Proper implant positioning is also extremely important to ensure that the implant is anchored within sufficient bone structure in the patient's jawbone.

The most common method for locating a dental implant hole is to visually survey the area and drill the hole in a freehand manner. However, this method can readily result in imperfect bores due to space limitations associated with working inside a patient's mouth. If the drilling axis is not properly chosen, the installed implants might cause damage to the tissues and muscle surrounding the area of implantation and subsequently cause temporary or permanent paresthesia. Furthermore, other problems can result from flawed or imperfect implant holes, such as uneven force distribution, insufficient bone growth around the implant, secondary infections, and ultimately, implant failure.

During a one-stage surgical procedure, a healing abutment assists in the healing, formation, and maintenance of the soft tissue over the implant while bone integration occurs. The healing abutment is immediately placed into the implant well to ensure that the gum line will heal properly and look natural once the final abutment is tapped into the implant.

During a two-stage surgical procedure, a cover screw is initially screwed into the implant well. The tissue surrounding the cover screw is then sutured to protect the implant site while bone integration occurs. Once the bone has integrated, an incision is made in the tissue above the site, at which time integration is checked. Once the bone has healed properly, the cover screw is then removed, and a healing abutment is screwed into the implant well. With the healing abutment securely in place the tissue surrounding the area is sutured. Approximately 4-6 weeks later, the healing abutment can be removed and a final abutment is then placed into the implant. In some surgical cases, a final abutment is immediately placed into the implant well rather than the healing abutment and sutures are not required. In both the one-stage and two-stage surgical procedure, the final abutment supports the final crown or denture.

Many types of surgical guides are on the market today. They can be tooth supported, gum supported, or bone supported. The simplest guides are done in the laboratory. They consist of acrylic templates (or stents), or teeth, both filled with radiopaque markers that provide the position of the teeth in relation to the bone on 2D radiographs. Holes are drilled through these surgical guides at the selected implant sites and the surgeon uses them to make bone perforations. Afterwards, the surgeon needs to raise a flap in order to make the osteotomies. More sophisticated guides use Ct-scan data and special software in order to place the implants according to three-dimensional (3D) data. The guide is then fabricated using stereolithographic machines or milling machines.

Each surgical stent commonly used is custom-built and these devices are only useful for a single patient, are costly to fabricate, and they require a number of intermediary office and laboratory steps to take an impression of the patient's arch and create a cast model from which the surgical stent is formed.

Superstructures are used as load-bearing elements that interface prosthesis to implants. In the conventional method for the construction of superstructures, a physical model of the patient's gums and dental implant heads is prepared on which the superstructure is built manually using molding and other techniques known in the art. The craftsman or technician skilled at manufacturing such dental superstructures takes into consideration the size and shape of the desired dentures to be placed over the superstructure when crafting the same. The procedure for manufacturing dental implant superstructures as is conventionally known in the art is time-consuming and sometimes results in imperfect structures or defects in the visual appearance of the dentures to be placed over the superstructure.

Therefore, in an effort to reduce costs and the number of steps associated with fabricating a traditional surgical stent, various forms of prefabricated surgical stents and positioning guide systems have been developed to aid the dental surgeon. In International patent application publication no. WO 94/26200, there is described an adjustable guiding device for positioning dental implants in which it is possible for the dental surgeon to adjust a drilling axis for each implant before proceeding to use the guiding device or drill template to guide the surgeon's drill for the purposes of preparing the drill hole for the implant.

In U.S. Pat. No. 5,401,170, there is disclosed a method and apparatus for measuring by camera image the implant heads of the implants in the patient's mouth for the purposes of cutting a frame on which the prosthetic teeth will be arranged and baked. In the method disclosed, the construction of the frame or superstructure is carried out in the absence of a reference to the shape and position of the patient's ideal tooth position.

Thus, as the dentures or artificial teeth are crafted on the frame or superstructure, care would be required during the manual process to ensure that the position of the teeth on the frame will match the opposed set of teeth in the patient's mouth.

It would thus be desirable to provide a drill guide system comprising components fabricated prior to the actual surgery that may be used more than once for the same patient, for any restoration configuration, and that enables precise implant spacing, and also ensures that the implant holes are drilled at the proper angle and orientation.

SUMMARY

In accordance with the present disclosure, it is disclosed dental prosthesis system comprising a prosthesis; a primary bar shaped to follow the anatomy of the patient's gum surface, the primary bar adapted to be received on the implants and to be used as at least one of a superstructure for supporting the prosthesis, a verification jig and an impression matrix, the primary bar having at least one aperture corresponding to the position of each implant hole in the patient's jawbone; and a base-plate having a shape adapted to be received on the patient's gum surface, comprising at least one hole each in alignment with a corresponding one of the aperture of the primary bar when the primary bar is seated on the base-plate, each hole of the base-plate corresponding to the position of each implant hole, the base-plate supporting the primary bar to form a drilling guide for guiding the drilling of implants holes in the patient's gum surface.

In an embodiment, the system further comprises at least one removable cylinder adapted to be secured to the primary bar in each aperture and having a diameter allowing insertion of the removable cylinder in each aperture of the primary bar, each removable cylinder securing the primary bar to each implant.

In another embodiment, the base-plate has a shape complementary to the shape of the primary bar to align the primary bar with respect to the implants during transformation of the primary bar into the superstructure, the verification jig or the impression matrix.

In another embodiment, the at least one removable cylinder forms the superstructure or the verification jig with the primary bar.

In an alternate embodiment, the drilling guide is manufactured as a single part including the primary bar and the base-plate.

In another embodiment, the system further comprises at least one transfer, the transfer shaped to be received in the aperture of the drilling guide, thereby forming the impression matrix with the primary bar and the base-plate when assembled.

In another embodiment, the system further comprises a final superstructure permanently installed in the patient's mouth, the final superstructure manufactured using the superstructure formed from the primary bar and the at least one removable cylinder.

Also encompass is the superstructure being manufactured as a single part.

In another embodiment, the at least one removable cylinder comprises an abutment portion contacting the implant when the superstructure is secured on the implants.

The at least one removable cylinder can further comprise an upper abutment portion and an abutment foot, the upper abutment portion and the abutment foot interconnecting to one another to form the removable cylinder.

In another embodiment, the system further comprises at least one fastener for securing the primary bar to each implant through the at least one removable cylinder.

In accordance with the present disclosure, it is also disclosed a method for securing a dental prosthesis in a patient mouth comprising providing a primary bar and a base-plate made as a function of patient's gum surface, the primary bar and base-plate concurrently defining at least one aperture corresponding to the position of each implant hole in the patient's jawbone; positioning the primary bar and base-plate as a drilling guide on the patient's gum surface; drilling at least one implant hole through the at least one aperture of the drilling guide in the jawbone; fixing each implant in each said implant hole; securing at least one cylinder to the primary bar to form a superstructure; and securing the prosthesis on the superstructure and the superstructure on the implants.

In an embodiment, the method further comprises positioning each implant through the aperture of the drilling guide in each of the implant hole.

In another embodiment, the method further comprises attaching the at least one cylinder to each implant through the aperture of the drilling guide In a further embodiment, the method further comprises installing the prosthesis over the drilling guide in order to precisely locate the drilling guide prior to drilling the at least one implant hole through the at least one aperture of the drilling guide in the jawbone.

In a further embodiment, the method further comprises positioning a transfer against each implant and securing each transfer to the drilling guide forming an impression matrix; removing the impression matrix from engagement to each implant; attaching an analog to each transfer; pouring a physical model with the impression matrix; and forming a final superstructure using the physical model prior to securing the prosthesis on the final superstructure and the final superstructure on the implants.

In a further embodiment, the method further comprises positioning the base plate and the primary bar on the patient's gum surface, positioning a cylinder against each implant and attaching each cylinder to the primary bar to form a verification jig to verify the precise location of the analogs on the physical model.

In a further embodiment, the method further comprises positioning the at least one cylinder to the primary bar to form the superstructure prior to securing the prosthesis on the superstructure; separating the base-plate from the superstructure; and forming a final superstructure with the superstructure to secure the final superstructure to the prosthesis and to the implants.

BRIEF DESCRIPTION OF THE DRAWINGS

Reference will now be made to the accompanying drawings, showing by way of illustration:

FIG. 2b illustrates a perspective view of the primary bar with implants connected on removable cylinders of FIG. 2a;

It will be noted that throughout the appended drawings, like features are identified by like reference numerals.

DETAILED DESCRIPTION

It is disclosed herein a dental implantation system that comprises components that can be used during surgical procedure and/or during prosthetic restoration.

Figure 1:
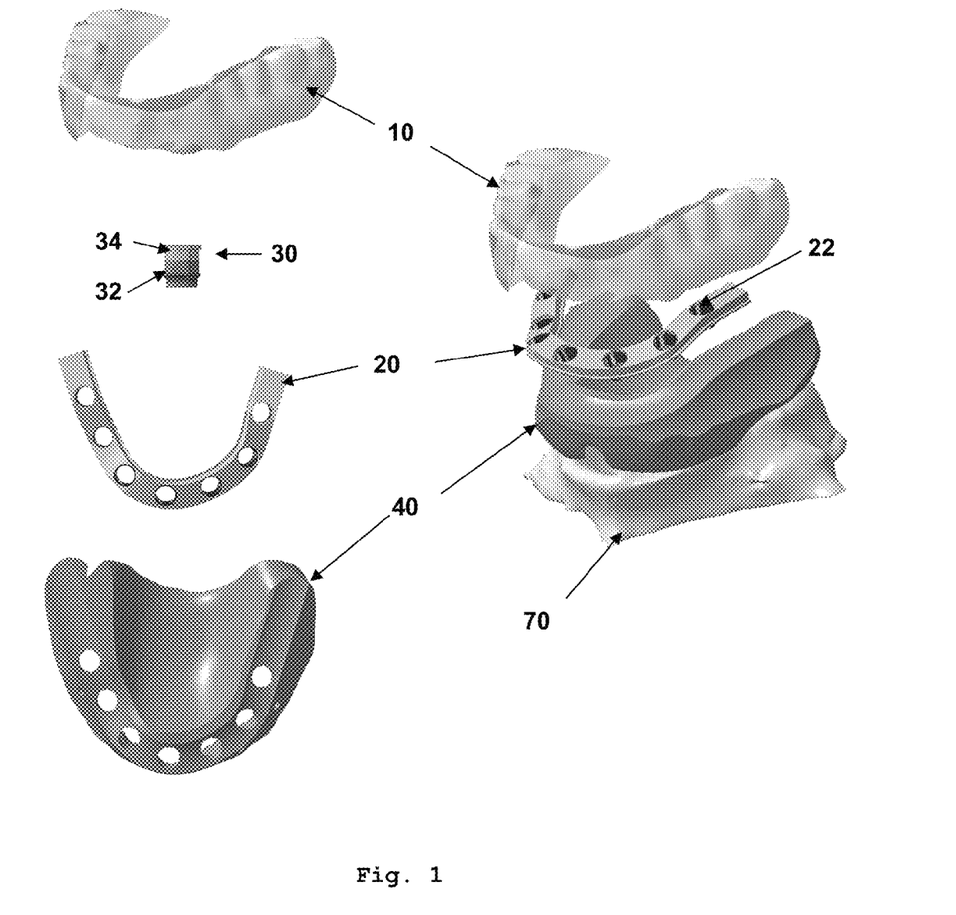
FIG. 1 illustrates an exploded view of components of a dental implant system described in the present disclosure.

As illustrated in FIG. 1, the dental implant system comprises a prosthesis 10, a primary bar 20, and a base-plate 40. When combined, these parts represent a replica of the patient's old prosthesis or wax-up of the future denture of the patient.

When combined to the base plate 40 and primary bar 20 (FIG. 3b), the prosthesis 10 is used to precisely position the drilling guide 60 into the patient mouth. The prosthesis 10 can be made of all materials allowing some resemblance to aesthetic teeth and gum, such as pink/white acrylic, plastic or porcelain.

Figure 3A:
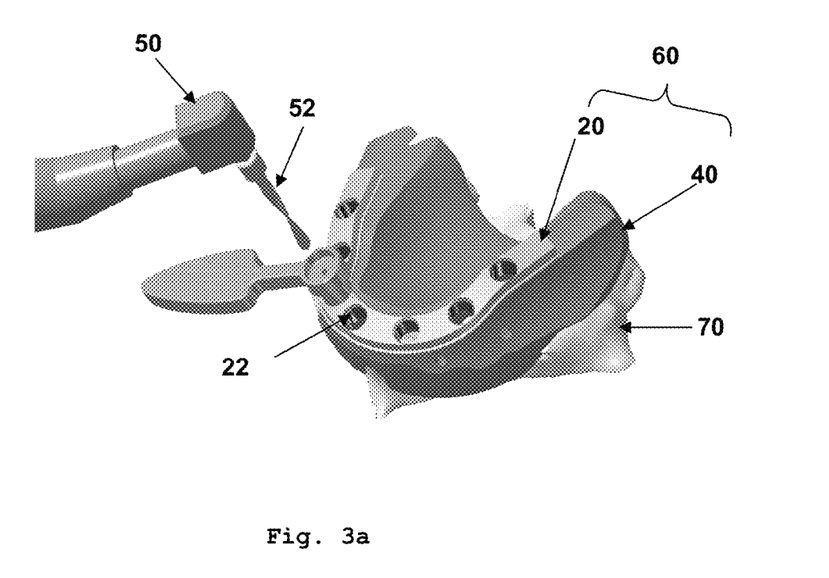
FIG. 3a illustrates a perspective view of the dental implant system of FIG. 1 used as a drilling guide.

The primary bar 20 disclosed herein is planed prior to the surgery as a function of computer 3D models of the patient's gum surface, dentures (e.g., patient's old prosthesis or wax-up of the future denture). Once it is positioned on the base-plate 40, the primary bar 20 becomes a drilling guide 60 that allows the dental surgeon to drill holes into the jawbone through each opening or implant abutment cavities of the primary bar 20 and corresponding holes in the base-plate 40 (FIG. 3a). The holes correspond to the location and orientation of the implant holes in the patient's real arch. The primary bar 20 can contain fixed cylinders 22 which serve as guides in the drilling steps. These fixed cylinders 22 can allow the primary bar 20 to be installed on the base-plate 40. The primary bar 20 can be prepared from any suitable material preventing corrosion of the primary bar 20, such as a solid piece of commercially pure titanium or any biocompatible material such as porcelain, zircon, resin and/or plastic.

When precision forming the primary bar 20, it is possible to use various techniques as described in U.S. Pat. No. 5,725,376. As an example, CNC milling in metal, molding techniques based of a master mold made of wax, or CAD/CAM techniques can all be used to fabricate the primary bar 20.

In one embodiment, the entire primary bar 20 is cut using a CNC milling machine programmed to cut according to the shape data specified using a computer model. In another embodiment, shape data is used to specify a 3-D wax or plastic model prepared using rapid prototyping techniques so that the primary bar 20 can then be cast. The model can be made of other materials such as, and not restricted to, in resin or acrylic for example. The casting metal may be titanium or any other suitable material. Alternatively, the primary bar 20 can be also manufactured directly by rapid prototyping techniques. In yet another embodiment, a CNC drilling machine could be equipped with a precision drill bit and used to provide a physical model with precisely-positioned implant abutment cavities. The shape of the primary bar 20 and cavities can be "crafted" manually. Such crafting can be guided by the computer model. The primary bar 20 can then be cast in the model and finished, with the abutments in precise position.

For conventional implant systems, the manufacturing of superstructure 80 normally requires measuring the actual implant position with reference to the gum surface. According to one embodiment of the present disclosure, a 3-D computer model of the primary bar is generated using 3-D models of the gum, implant 36 heads and teeth acquired from medical images or 3D acquisition techniques (e.g. using a 3D coordinate measuring machine). Also, the original drill hole position data is then measured and provided with the 3-D computer model in order to reduce the shifts between the desired and the actual implant 36 positions.

A medical image of the jawbone and tissue structure is obtained by using x-ray imaging or nuclear imaging techniques to produce a three-dimensional model which has a reference to the gum surface or some other fixed reference with respect to the patient's jawbone. Preferably, a radiographic scanner guide, or the patient's old denture, is used which is molded to conform to the shape of the patient's gums and which includes radio-opaque spheres whose positions with respect to the patient's jawbone can be referenced.

Selection of the drilling holes positions using the model is transferred to a CNC device for the purposes of providing the positions of the apertures in the primary bar 20.

Preferably, the dental surgeon will select the position for each implant drill hole, not only to position the implant 36 in the optimum location within the jawbone, but also to select a position of support which is suitable for supporting the prosthesis 10. Therefore, it is preferred to display, in addition to the three-dimensional computer graphics model of the jawbone 70, the patient's dentures in the proper spatial relationship with respect to the jawbone 70. This requires imaging the patient's dentures or teeth, and possibly gum structure, in addition to the jawbone 70, in such a way that all images are referenced with respect to one another to be integrated into the same three-dimensional computer graphics model.

The base-plate 40 is used to support the primary bar 20 as a drilling guide 60 (FIG. 3a). The base-plate 40 is positioned over the anatomical structure (or jawbone 70) of the patient when drilling. The base-plate 40 is shaped to allow it to be securely seated on the patient's gum surface, jawbone 70 or teeth, comprises holes corresponding in alignment to the opening or implant abutment cavities or apertures of the primary bar 20. The holes in the base-plate 40 are in fluid communication with the apertures of the primary bar 20 and are also of sufficient diameter to allow the drill 50 and implants 36 to pass therethrough. The base-plate 40 can be fixed to the supporting anatomical structure 70 of the patient by screws or stem. The base-plate 40 is manufactured in plastic or resin for example.

Figure 2A:
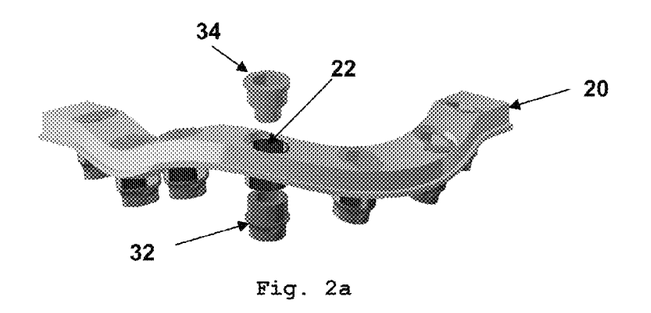
FIG. 2a illustrates a perspective view of a primary bar of the dental implant system of FIG. 1.
Figure 2B:
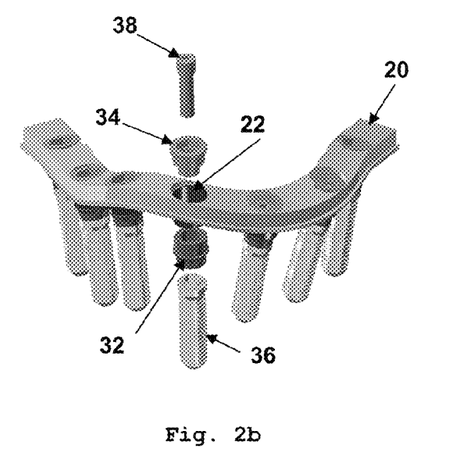
Figure 2C:
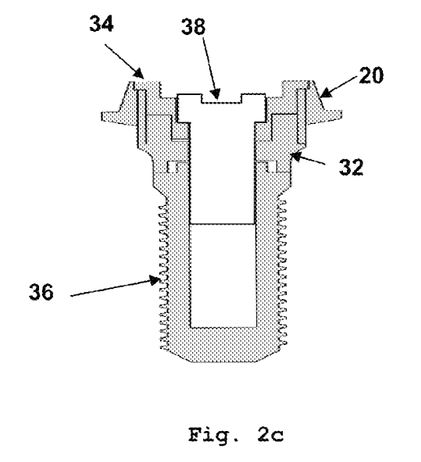
FIG. 2c illustrates a sectional view of one of the implants of FIG. 2b fixed on one of the removable cylinders.
Figure 2D:
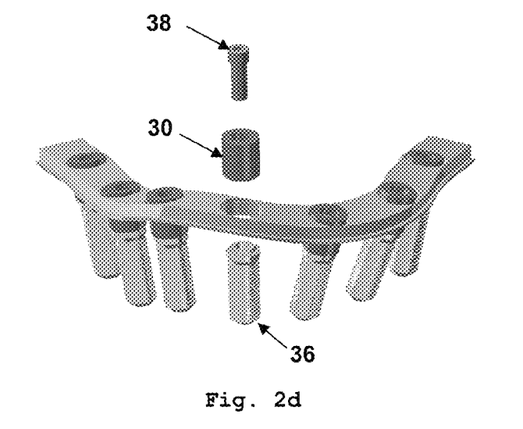
FIG. 2d illustrates a perspective view of one of the implants of FIG. 2b fixed on one of the removable cylinders, the removable cylinders being glued to the primary bar.
Figure 4A:
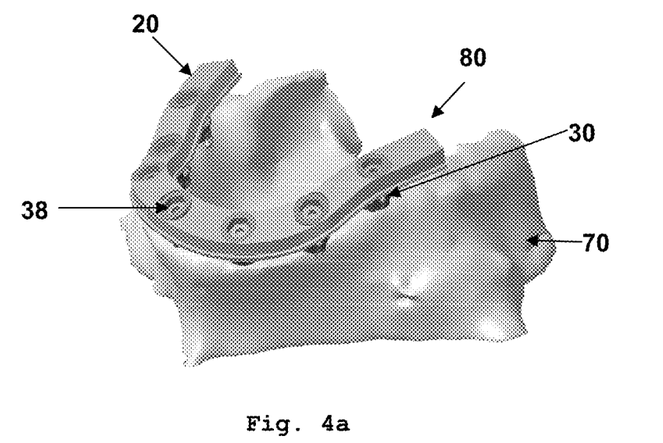
FIG. 4a illustrates a perspective view of the primary bar of FIG. 2a used as a superstructure or a verification jig.

As illustrated in FIG. 4a, in a further embodiment, removable cylinders 30, once connected to the primary bar 20, allow using the primary bar 20 as a superstructure or as a verification jig during the prosthetic restoration step. The primary bar 20 is shaped to follow the anatomy of the patient's gum surface, and can be used as a superstructure, to rigidly link the implants and support the patient's prosthesis, or as a verification jig, to verify the precision of the physical model (replica of the patient mouth including implants). The removable cylinders 30 can be for example screwed on the primary bar 20. The removable cylinders 30 are made of resistant materials such as titanium, plastic, gold or steel and contain an upper abutment 34 and an abutment foot 32 (FIG. 2a). The upper abutment 34 can have an external threading and the abutment foot 32 can comprise an internal threading. Alternatively, the removal cylinders can be made of only one piece, which is fixed to the primary bar 20 when used as a superstructure or verification jig as described herein, for example but not limited to, in a snap-fitted manner, glued, welded or screwed on the implant abutment cavities or apertures (FIG. 2d). Alternatively, the removable cylinders could be milled and directly integrated as a part of the implant, and attached to the primary bar with any of the fixating system described hereinabove.

Different combinations of the disclosed components of the multi-functional dental implantation system described therein are used during chirurgical procedure and/or during prosthetic restoration.

Firstly, when the surgeon wishes to be provided with a drilling guide 60, as illustrated in FIG. 3a, the primary bar 20 is positioned over the base-plate 40 as a drilling guide 60 and the implant abutment cavities or apertures of the primary bar 20 and the apertures of the base-plate 40 allow guiding the drilling rod 52 extending from the drill 50 with precision in its position and orientation during drilling. The drilling guide 60 is used to guide the drilling of the holes, but also ensures precision when inserting the implants 36 in the holes. Alternatively, a person skilled in the art will understand that the implants 36 are inserted through the openings of the primary bar 20 and base-plate 40 and the alignments of the corresponding openings in the primary bar 20 and base-plate 40 also ensures precision when inserting the implants 36. The base-plate 40 also supports the primary bar to form the drilling guide 60 therewith to position or reference the primary bar with respect to the implants during the process of transforming the primary bar into a temporary or final superstructure or a verification jig.

Figure 3B:
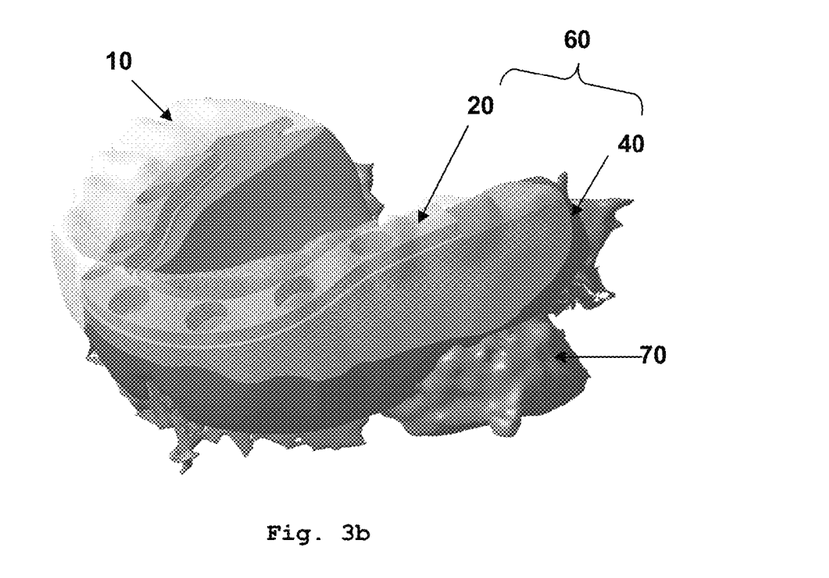
FIG. 3b illustrates a perspective view of the dental implant system used in order to position the drilling guide of FIG. 3a within the mouth of the patient prior to surgery or to articulate the master model with the opposite teeth/denture model following surgery.
Figure 3C:
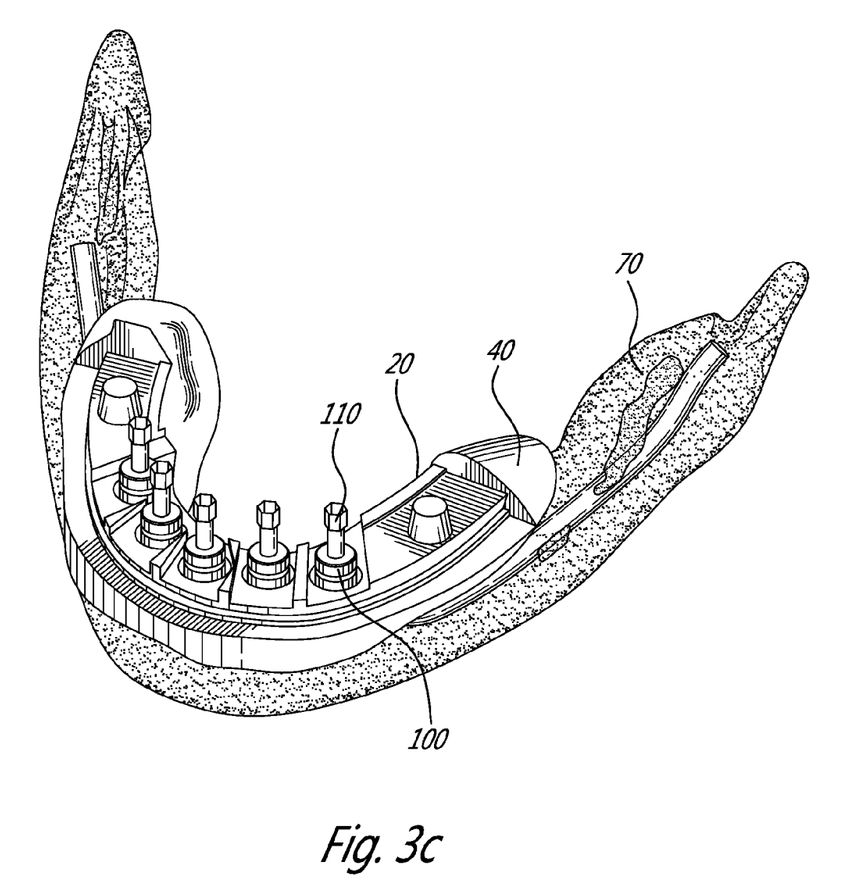
FIG. 3c illustrates a perspective view of the drilling guide of FIG. 3a showing the transfers inside the apertures of the drilling guide, thus forming an impression matrix.
Figure 3D:
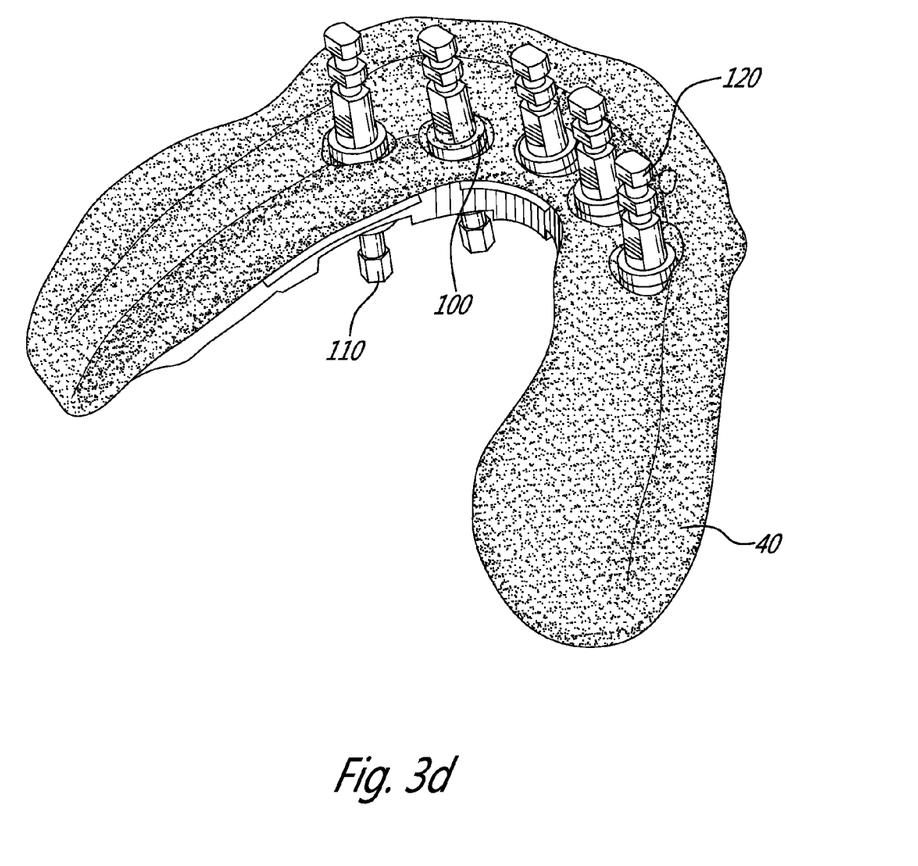
FIG. 3d illustrates a perspective view of the impression matrix of FIG. 3d showing the implant analogs connected to the transfers. The analogs are fixed to the transfers with screws.

Before drilling the holes, the surgeon can place the half-prosthesis 10 over the primary bar 20 and the base-plate 40 in the mouth of the patient in order to precisely locate the drilling guide 60 and insert the retention screws or pins, thus stabilizing the entire drilling guide 60 (FIG. 3b).

As can be appreciated, the dental surgeon prepares the implant holes using the drilling guide 60 by removing circular portions of the gum (gingival taps) at the implant sites.

Following insertion of the implants into the anatomical structure 70, the primary bar 20 and the base-plate 40 can be used as an impression matrix. Using long transfers, the doctor can inject impression material between these transfers and fix the transfers in order to capture the precise relationship of the implants 36 to the drilling guide 60. Then analogs, corresponding to replica of the implants, are screwed to the transfers and the model is poured in stone in order to create a replica of the patient mouth with the implants (also known as physical model, stone model or master model).

In addition, once the implants 36 are positioned, the primary bar 20 can be used as a superstructure 80 in order to install temporarily if necessary the prosthesis 10, the superstructure 80 consisting of the primary bar 20 on which removable cylinders 30 have been fixed in order to allow the primary bar to act as an interface between implant(s) 36 and prosthesis 10 (FIG. 4a).

The removable cylinders 30 can be connected on the primary bar 20 by a fastener such as being snapped, glued, welded, attached for example, and without being limited to. The removable cylinders 30 connect the implant 36 to the primary bar 20 through the fixed cylinders 22 or apertures, and can allow the position of the implants 36 to be verified. The removable cylinders 30 can be retained by screw 38 to the implants (FIGS. 2b, 2c, 2d and 4a).

Figure 4B:
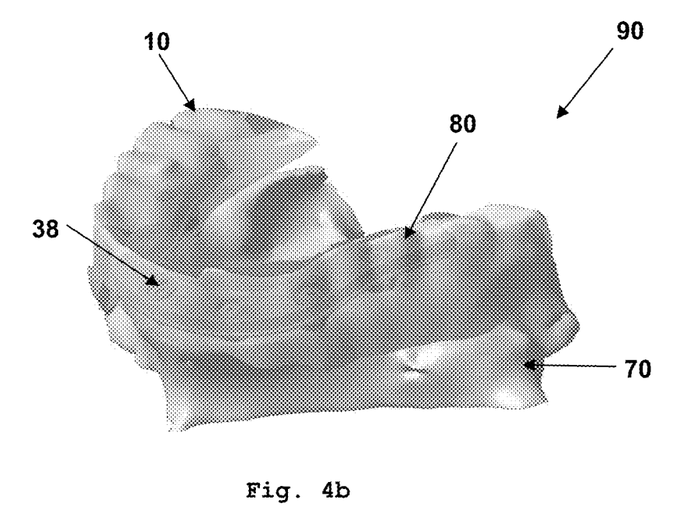
FIG. 4b illustrates a perspective view of the primary bar of FIG. 4a used as a superstructure with a prosthesis used as a temporary or final prosthesis.

Furthermore, the surgeon or dental technician can also use the primary bar 20 as part of a superstructure 80 and temporary prosthesis 90 or final prosthesis once the prosthesis 10 is fixed to the superstructure 80 (FIG. 4b). The prosthesis 10 can be fixed on the superstructure 80, and both attached to the implants 36, or alternatively, the superstructure 80 is fixed to the implants 36 and the prosthesis is subsequently attached to the superstructure 80. Removable cylinders 30 can be added to the primary bar 20 for securing the superstructure 80 on the implants 36. The surgeon or dental technician will install the base-plate 40 and the primary bar 20 in the mouth of the patient or on the physical model, fixing afterwards the removable cylinders 30 to the primary bar 20. The base-plate 40, primary bar 20 and removable cylinders 30 are removed from the mouth of the patient or from the physical model, leaving the removable cylinders 30 fixed to the primary bar 20, allowing connecting to at least one implant 36, forming the superstructure 80, which can be a temporary superstructure 80 or a final superstructure 80. The temporary superstructure 80 can be used to cast the final superstructure 80 if necessary.

For clarity purposes, a superstructure 80 is intended herein to mean the primary bar 20 on which removable cylinders 30 have been fixed in order to allow the primary bar to act as an interface between implant(s) 36 and prosthesis 10.

A drilling guide 60 is intended to correspond to the primary bar 20 positioned over the base-plate 40, allowing the surgeon to be guided during drilling.

A verification jig is intended to correspond to the primary bar 20, for instance with the removable cylinders 30, allowing using the primary bar 20 as a verification jig during the prosthetic restoration step.

The dental implantation system disclosed herein which can thus be used during surgical procedure and/or during prosthetic restoration to reduce costs and the number of steps associated with fabricating each of the components since the individual components can be used in combination as a superstructure 80, a drilling guide 60, a verification jig, an impression matrix, a temporary prosthesis 90 or final prosthesis without need to manufacture separately such tools used by the surgeon.

The prosthesis 10, primary bar 20 and base plate 40 have novel multi-functions for dental implantation as disclosed herein. In addition, the system allows the surgeon to proceed to more efficient surgeries (e.g. a one-day surgery), which reduces the time spent by the patient in surgery and accelerates healing. Because all the components of the system disclosed herewith are not only custom-fitted and there is no need to manufacture all normal tools used by the surgeon since the components can be combined to act as a superstructure 80, a drilling guide 60, a verification jig, an impression matrix or a temporary prosthesis 90/final prosthesis, the waiting time for the manufacture of the components is also greatly reduced.

According to another aspect of the present disclosure, there is provided a method for implanting dental implants in a patient comprising the steps of scanning the patient's jawbone and old prosthesis (or wax-up of the future denture); obtaining and referencing 3D computer models of the patient's jawbone and old prosthesis (or wax-up of the future denture); virtually planning the surgery; designing the primary bar 20, the base-plate 40, and prosthesis 10; manufacturing the base-plate 40 and primary bar 20; manufacturing the prosthesis 10; and proceeding to the surgery and prosthetic restoration.

The virtual planning of the surgery involves creating a three-dimensional model of a patient's gum, jawbone, tissue structure and prosthesis from medical images of the jawbone, tissue structure and prosthesis obtained by using x-ray imaging, or possibly nuclear imaging techniques (e.g., for graphic use) and/or 3D acquisition techniques (e.g. using a 3D coordinate measuring machine). The three-dimensional graphic computer model is used to select a number of virtual implant drill holes positions in order to optimize their position, dimension, orientation and depth.

The step of manufacturing the primary bar 20 involves precision techniques as described in U.S. Pat. No. 5,725,376. As an example, computer-controlled CNC milling in metal, or CAD/CAM techniques may be used to manufacture the primary bar 20. For manufacturing the primary bar 20, virtual planning of the position of the implants 36 is taken into consideration, as well of the position of removable cylinders 30 and fixed cylinders 22, if needed. Rapid prototyping techniques are also envisioned in order to manufacture the primary bar 20 ultimately once appropriate materials are discovered.

The design of the base-plate 40 is accomplished by using the 3D computer model of the primary bar 20, and material above including the teeth, to the 3D computer model of the patient's old or future prosthesis (dental implantation system). The manufacturing of the prosthesis 10 and base-plate 40 is accomplished by using techniques known in the art, also encompassing CAD/CAM techniques and rapid prototyping, and the primary bar 20 and base-plate 40 produced in the previous step in order to ensure precision and consistency.

The drilling guide 60 can be made as mentioned hereinabove by securing the primary bar 20 to the base-plate 40, or by manufacturing both parts as a single drilling guide 60.

Once confirmation that the multi-functional system is adapted for the patient, the surgeon uses the drilling guide 60 as described hereinabove in order to drill the implant holes by removing circular portions of the gum (gingival taps) at the implant sites. Once the holes have been drilled, the surgeon inserts the implants 36 in the holes, by passing through the drilling guide 60 for precision. The surgeon removes the drilling guide 60 and proceeds to the prosthetic restoration. The primary bar 20 which was used as part of the drilling guide 60 can also be used as the temporary or final superstructure 80 for supporting prosthesis 10 when used as a temporary prosthesis 90 or final dental prosthesis. Finally, the base-plate 40 is removed separately and the prosthesis 10 is secured on the superstructure 80, and the superstructure 80 is secured on the implants 36. Alternatively, the superstructure 80 is fixed to the implants 36 and the prosthesis is subsequently attached to the superstructure 80.

In addition, the primary bar 20 and the base-plate 40 can be used as an impression matrix as described hereinabove, using long transfers, to inject impression material between these transfers in order to capture the precise relationship of the implants 36 to the drilling guide 60. Then analogs are fixed, such as screwed, to the transfers and the model is poured in stone in order to create a replica of the patient mouth with the implants (physical model).

The verification jig as disclosed herein can subsequently be used prior to manufacturing the final prosthesis or temporary prosthesis 90 to verify the precision of the analogs on the physical model.

The base plate 40 and the primary bar 20 are installed on the physical model and the removable cylinders 30 are fixed on analogs through the aperture of the primary bar 20 and the base-plate 40, the removable cylinders 30 being ultimately fixed to the primary bar 20 to form a temporary superstructure 80. The base-plate 40 is then removed and the temporary superstructure 80 is used to form the final superstructure 80 by techniques known in the art, such as by casting, CAD/CAM techniques, rapid prototyping, or duplicating technique for example. The prosthesis 10 is then secured on the final superstructure 80, and the final superstructure 80 is secured on the implants 36.

While the invention has been described with particular reference to the illustrated embodiment, it will be understood that numerous modifications thereto will appear to those skilled in the art. Accordingly, the above description and accompanying drawings should be taken as illustrative of the invention and not in a limiting sense.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:

1. A dental prosthesis system comprising:
   a primary bar shaped to follow the anatomy of a patient's gum surface, the primary bar adapted to be received on implants and to be used as at least one of a superstructure and a verification jig, the primary bar having at least one aperture corresponding to a position of an implant hole in the patient's gum surface;
   a prosthesis which is seatable on the primary bar and the primary bar seatable on a base-plate to form the dental prosthesis system; and
   a base-plate comprising at least one hole each in alignment with a corresponding one of said aperture of the primary bar when the primary bar is seated on the base-plate, each hole of the base-plate corresponding to the position of each implant hole, the base-plate supporting the primary bar to form a drilling guide for guiding the drilling of implants holes in the patient's gum surface.

2. The dental prosthesis system according to claim 1, further comprising at least one removable cylinder adapted to be secured to the primary bar in each aperture and having a diameter allowing insertion of said removable cylinder in each aperture of the primary bar, each removable cylinder securing the primary bar to each implant.

3. The dental prosthesis system according to claim 1, wherein said base-plate has a shape complementary to the shape of the primary bar to align the primary bar with respect to the implants during transformation of the primary bar into the superstructure or the verification jig.

4. The dental prosthesis system according to claim 2, wherein said at least one removable cylinder forms the superstructure or the verification jig with the primary bar.

5. The dental prosthesis system according to claim 1, wherein the drilling guide is manufactured as a single part including the primary bar and the base-plate.

6. A method for securing a dental prosthesis on a patient jawbone comprising:
   providing a primary bar and a base-plate made as a function of patient's gum surface, the primary bar and base-plate concurrently defining at least one aperture corresponding to a position of an implant hole in the patient's jawbone;
   positioning the primary bar and base-plate as a drilling guide on the patient's gum surface using a prosthesis to articulate the drilling guide with the opposite denture of the patient;
   inserting screws or pins to secure the drilling guide on the patient jawbone;

removing the prosthesis;
drilling at least one implant hole through the at least one aperture of the drilling guide in the jawbone;
fixing an implant in each said implant hole;
securing at least one cylinder to the primary bar to form a superstructure or a verification jig; and
securing the prosthesis on the superstructure and the superstructure on the implants.

7. The method according to claim 6, further comprising positioning each implant through the aperture of the drilling guide in each said implant hole.

8. The method according to claim 6, further comprising attaching the at least one cylinder to each implant through the aperture of the drilling guide.

9. The method according to claim 6, further comprising installing the prosthesis over the drilling guide in order to precisely locate the drilling guide prior to drilling the at least one implant hole through the at least one aperture of the drilling guide in the jawbone.

10. The method according to claim 6, further comprising:
positioning a transfer against each implant and securing each transfer to the drilling guide forming an impression matrix;
removing the impression matrix from engagement to each implant;
attaching an analog to each transfer;
pouring a physical model with the impression matrix; and
forming a final superstructure using the physical model prior to securing the prosthesis on the final superstructure and the final superstructure on the implants.

11. The method according to claim 10, further comprising positioning the base plate and the primary bar on the patient's gum surface, positioning a cylinder against each implant and attaching each cylinder to the primary bar to form the verification jig to verify the precise location of the analogs on the physical model.

* * * * *